(12) United States Patent
Castillo et al.

(10) Patent No.: US 8,292,491 B2
(45) Date of Patent: Oct. 23, 2012

(54) FLEXIBLE BAG, MIXING SYSTEM AND METHOD FOR FIXING A FLEXIBLE BAG INSIDE A RIGID CONTAINER

(75) Inventors: Jose Castillo, Brussels (BE); Florence Bosco, Mignault (BE)

(73) Assignee: Artelis S.A., Brussels (BE)

( * ) Notice: Subject to any disclaimer, the term of this patent is extended or adjusted under 35 U.S.C. 154(b) by 650 days.

(21) Appl. No.: 12/444,049

(22) PCT Filed: Apr. 24, 2007

(86) PCT No.: PCT/EP2007/054000
§ 371 (c)(1),
(2), (4) Date: Apr. 2, 2009

(87) PCT Pub. No.: WO2008/040569
PCT Pub. Date: Apr. 10, 2008

(65) Prior Publication Data
US 2010/0215290 A1    Aug. 26, 2010

(30) Foreign Application Priority Data

Oct. 3, 2006 (WO) .................. PCT/EP2006/066980
Apr. 12, 2007 (WO) .................. PCT/EP2007/053595

(51) Int. Cl.
*B01F 13/08* (2006.01)
(52) U.S. Cl. ...................................... 366/273
(58) Field of Classification Search ............ 366/273
See application file for complete search history.

(56) References Cited

U.S. PATENT DOCUMENTS

| | | |
|---|---|---|
| 3,002,895 A | 10/1961 | Freedman |
| 3,647,397 A | 3/1972 | Coleman |
| 3,962,892 A | 6/1976 | Garlinghouse |
| 4,162,855 A | 7/1979 | Bender |
| 4,209,259 A | 6/1980 | Rains |
| 4,356,967 A | 11/1982 | Lunick |
| 4,498,785 A | 2/1985 | de Bruyne |
| 4,668,632 A | 5/1987 | Young et al. |
| 4,711,582 A | 12/1987 | Kennedy |
| 4,783,172 A | 11/1988 | Garg |
| 4,808,348 A | 2/1989 | Rudick et al. |
| 4,978,616 A | 12/1990 | Gaffar |
| 5,061,448 A | 10/1991 | Mahe et al. |
| 5,270,207 A | 12/1993 | Matsumura et al. |
| 5,501,971 A | 3/1996 | Carll |

(Continued)

FOREIGN PATENT DOCUMENTS

DE    32 46 330 A1    6/1984
(Continued)

OTHER PUBLICATIONS

Annotated Figure 1 of Stewart, US 5941635.*

(Continued)

*Primary Examiner* — Walter D Griffin
*Assistant Examiner* — Christopher Vandeusen
(74) *Attorney, Agent, or Firm* — King & Schickli, PLLC

(57) ABSTRACT

Flexible bag includes at least a first wall, a second wall facing the first wall when the flexible bag is folded and a functional part having at least a portion protruding from the first wall inside the bag. The second wall includes protective means intended to prevent damage to the flexible bag and/or to the functional part.

14 Claims, 2 Drawing Sheets

U.S. PATENT DOCUMENTS

Figure 1:
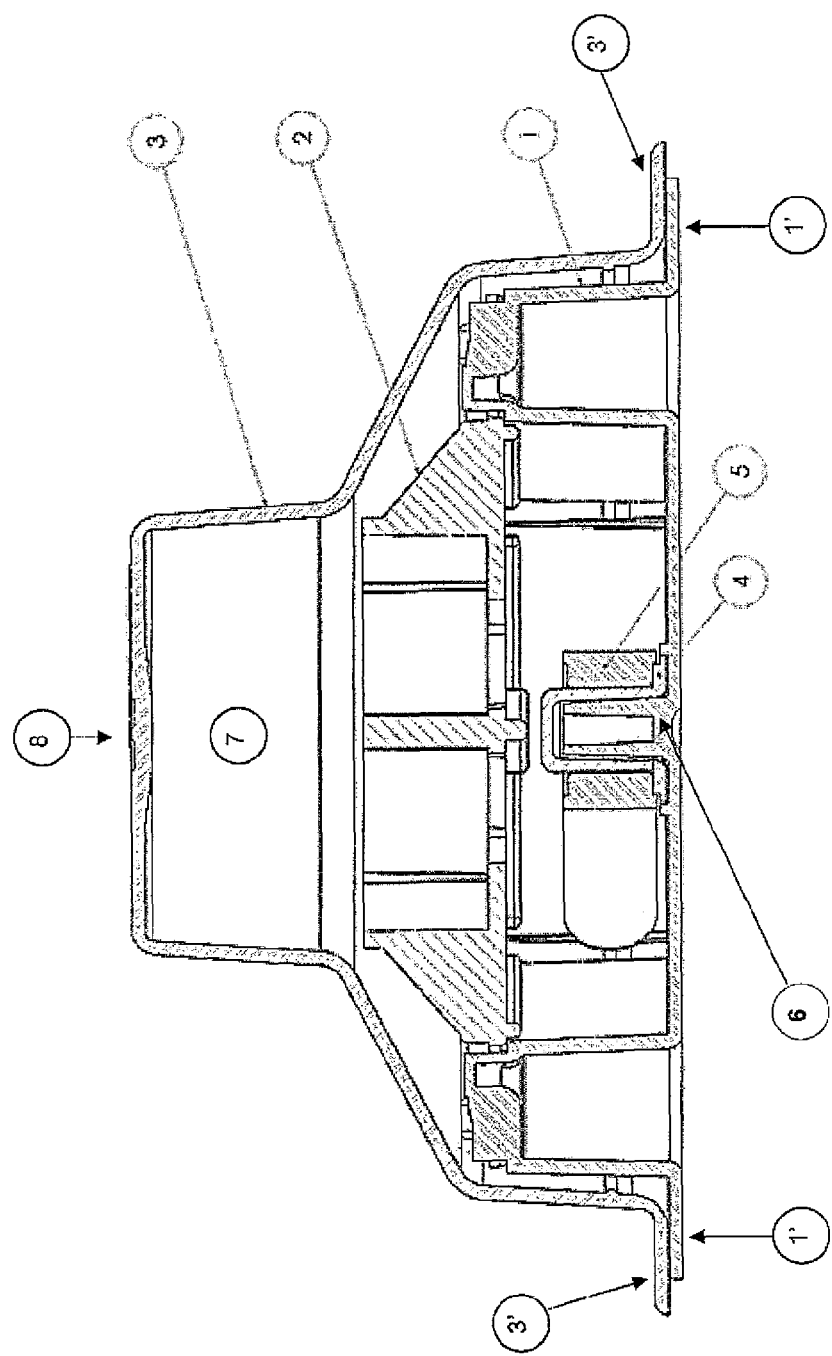

| | | | |
|---|---|---|---|
| 5,727,878 A | 3/1998 | Sullivan, Jr. | |
| 5,750,440 A | 5/1998 | Vanell et al. | |
| 5,779,359 A | 7/1998 | Gambrill | |
| 5,803,137 A | 9/1998 | Shimotoyodome et al. | |
| 5,941,635 A | 8/1999 | Stewart | |
| 5,988,422 A | 11/1999 | Vallot | |
| 6,071,005 A | 6/2000 | Ekambaram et al. | |
| 6,245,555 B1 | 6/2001 | Curtis | |
| 6,247,840 B1 | 6/2001 | Gaffar | |
| 6,494,613 B2 * | 12/2002 | Terentiev | 366/279 |
| 6,670,171 B2 | 12/2003 | Carll | |
| 7,153,021 B2 | 12/2006 | Goodwin et al. | |
| 7,278,780 B2 * | 10/2007 | Goodwin et al. | 366/273 |
| 2001/0039369 A1 | 11/2001 | Terentiev | |
| 2002/0082173 A1 | 6/2002 | Terentiev | |
| 2002/0091371 A1 | 7/2002 | Ritter | |
| 2002/0105856 A1 | 8/2002 | Terentiev | |
| 2002/0145940 A1 | 10/2002 | Terentiev | |
| 2003/0226857 A1 | 12/2003 | Bibbo et al. | |
| 2004/0047232 A1 | 3/2004 | Terentiev | |
| 2004/0062140 A1 | 4/2004 | Cadogan et al. | |
| 2004/0218468 A1 | 11/2004 | Terentiev | |
| 2004/0221897 A1 | 11/2004 | Schubmehl et al. | |
| 2004/0252582 A1 | 12/2004 | Bucher | |
| 2005/0002274 A1 | 1/2005 | Terentiev | |
| 2005/0117449 A1 | 6/2005 | Terentiev | |
| 2005/0127215 A1 | 6/2005 | Lienhart et al. | |
| 2005/0201201 A1 | 9/2005 | Terentiev | |
| 2006/0092761 A1 | 5/2006 | Terentiev | |
| 2006/0131765 A1 | 6/2006 | Terentiev et al. | |
| 2007/0030759 A1 | 2/2007 | Terentiev | |
| 2007/0201993 A1 | 8/2007 | Terentiev et al. | |
| 2007/0220956 A1 | 9/2007 | Terentiev | |
| 2007/0252290 A1 | 11/2007 | Terentiev et al. | |
| 2007/0263484 A1 | 11/2007 | Terentiev | |
| 2008/0008028 A1 | 1/2008 | Terentiev et al. | |

FOREIGN PATENT DOCUMENTS

| | | |
|---|---|---|
| DE | 38 18776 A1 | 7/1989 |
| DE | 19542227 | 5/1997 |
| DE | 19705118 | 8/1998 |
| DE | 201 14 076 | 10/2001 |
| EP | 0033292 | 8/1981 |
| EP | 0200792 | 11/1986 |
| EP | 0343885 | 11/1989 |
| EP | 0 433 463 A1 | 6/1991 |
| EP | 0590 473 | 4/1994 |
| EP | 1 462 155 A1 | 9/2004 |
| GB | 2 076 677 A | 12/1981 |
| GB | 2202549 | 9/1988 |
| JP | 61-067476 | 4/1986 |
| JP | 61212275 | 9/1986 |
| JP | 631626 | 1/1988 |
| JP | 63-36825 | 2/1988 |
| JP | 03-242297 | 10/1991 |
| JP | 6153902 | 6/1994 |
| JP | 10313718 | 12/1998 |
| JP | 10314569 | 12/1998 |
| WO | WO9833538 | 8/1998 |
| WO | WO0011953 | 3/2000 |
| WO | WO 2005/037658 A2 | 4/2005 |
| WO | WO2005068059 * | 7/2005 |
| WO | WO 2005/118771 A2 | 12/2005 |
| WO | WO 2006/002091 A2 | 1/2006 |
| WO | WO 2006/063087 A2 | 6/2006 |
| WO | WO 2007/039600 A1 | 4/2007 |
| WO | WO 2008/040567 A1 | 4/2008 |
| WO | WO 2008/040568 A1 | 4/2008 |

OTHER PUBLICATIONS

ATMI, Inc., ATMI LifeSciences Newmix™ Jet-Drive™ is Your Benchmark for Disposable, Contained, Ultra-Clean Mixing, Launch of Revolutionary Mixing Technology, Apr. 16, 2007, pp. 1-2, Hoegaarden, Belgium.

Bosco et al., ATMI completes its NEWMIX™ range with ARTELIS™ single-use mixing technology, pp. 1, posted publicly exhibited at Bioproduction Dublin Conference, Dublin, Ireland, Oct. 24, 2006.

GE Healthcare Life Sciences—WAVE Bioreactor Home, WAVE Bioreactor Systems, http://www4.gelifesciences.com/APTRIX/upp01077.nsf/Content/wave_bioreactor_home, pp. 1-2, downloaded Jan. 4, 2010, General Electric Co., Schenectady, New York.

Hyclone Americas, Mixtainer™, An integrated single-use sterile system for mixing and maintaining homogenous aqueous solutions, pp. 1-2, believed to be available at least as early as Jul. 12, 2007.

Disposable Bioreactors Gaining Favor, New Components and Systems Improve Process Reliability and Reduce Cost, Genetic Engineering & biotechnology News, Jun. 15, 2006, vol. 26, No. 12, pp. 1-8.

Russ Musch, Product Brief Form for HyClone Bioprocess Containers, May 31, 2001, pp. 1-3.

LevTech, Inc. Business Plan, Sep. 5, 2000, pp. 1, 8-9, 11-13, 25.

Mechanical drawing of Bottom Drain Barrel believed to have been sold by Hyclone Laboratories, Inc., at least as early as Jan. 2002, as cited in US 7,278,780.

ATMI Newmix®-Levtech® Disposable Mixing and Storage Systems, ATMI, Danbury, CT downloaded from www.atmi-lifesciences.com/html/newmix.html on Jan. 4, 2010.

Pending claims in U.S. Appl. No. 12/444,040, filed Apr. 2, 2009 (national stage of PCT/EP07/53998).

United States Postal Service, Mailing Standards of the United States Postal Service Publication 52—Hazardous, Restricted, and Perishable Mail, Jul. 1999, p. 315.

Schoeb, A Bearingless Motor for a Left Ventricular Assist Device, 7th International Symposium on Magnetic Bearings, Zurich, Switzerland, Aug. 23-25, 2000.

* cited by examiner

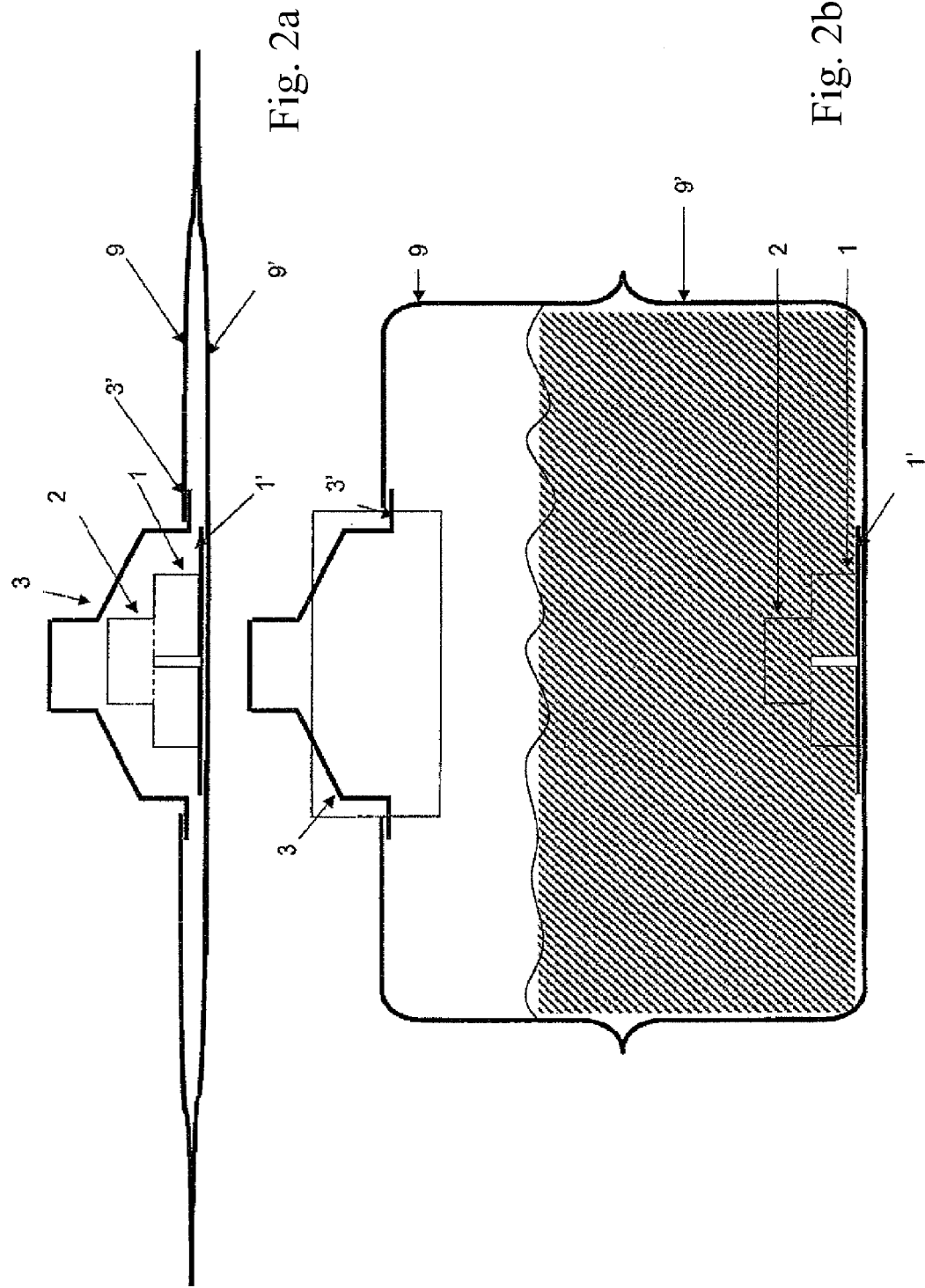

FLEXIBLE BAG, MIXING SYSTEM AND METHOD FOR FIXING A FLEXIBLE BAG INSIDE A RIGID CONTAINER

The present application is a national stage entry, under 35 USC 371, of PCT International Patent Application Number PCT/EP2007/054000 filed on 24 Apr. 2007, which claims priority to International Patent Application Number PCT/EP2007/053595 filed on 12 Apr. 2007 and International Patent Application Number PCT/EP2006/066980 filed on 3 Oct. 2006. The complete disclosures of the aforesaid International Patent Application Numbers PCT/EP2007/054000, PCT/EP2007/053595, and PCT/EP2006/066980, including the International Publication Number WO2008/040569, are expressly incorporated herein by reference in their entireties for all purposes.

The present invention relates to a flexible bag; to a mixing system comprising such a flexible bag and to a method for fixing a specific flexible bag into a rigid container.

The storage, mixing and/or suspension of solutions is required in many technical fields such as biotechnology, pharmaceuticals and medical.

For example, in the field of the biotechnology and pharmaceutical industry, it is often necessary to prepare and to complement solutions, buffers, culture medium, suspensions, etc (referred to in general terms hereinafter as liquid substances) and to store these solutions. Some specific applications include dilution, dissolution and/or adjusting and/or measuring pH, salinity conditions, concentration, osmolality, temperature . . . of a liquid substance of any kind (buffer, culture medium, saline solution, etc)

To be safe and effective for their intended use, solutions of culture media, buffers, reagents, etc used in these fields must be pure and sterile. Accordingly, the mixing tank, mixing device, storage bag and all other reusable components that contact the solution must be carefully cleaned after use to avoid any cross contamination with subsequent batches of solutions. The cleaning of the structural components is labour-intensive, time-consuming, and costly.

In order to avoid these cleaning steps, single use flexible bags have been developed. These are disposable flexible bags intended to be supported in rigid containers and provided with functional parts like a mixing device, sensors, dip tubes . . . and generally intended to be supported in a rigid container. Advantageously, the mixing devices used in these bags are magnetic devices driven by an external driver positioned outside of the bag and may be part of or fixed to the rigid container. By doing so, there is no risk of contamination of the contents of the bag from the outside.

However, such mixing device and other functional parts generally protrude inside the bag so that in the case said bag has a flexible wall facing the protruding part, said wall can be damaged by the protrusion before it is filled.

Besides, in some circumstances, inserting the flexible bag into a rigid container is not easy namely because said bag is not easy to handle and/or because some parts must be connected with parts of the container.

Finally, some functional parts are not fixed inside the bag so that they need to be kept in place during shipping and handling of the bag when it is empty.

The present invention aims at solving these problems by providing a system where the flexible bag is prevented from being damaged by a part protruding inside of it; where if said part is not fixed to the bag, it is kept in place during storage and handling of the empty bag; and where said bag is easier to install inside a rigid container.

Accordingly, the present invention relates to a flexible bag comprising at least a first wall, a second wall facing the first wall when the flexible bag is folded and at least one functional part having at least a portion protruding from the first wall inside the bag, wherein the second wall comprises protective means intended to prevent damage to said flexible bag and/or to said functional part.

According to the invention, the terms "flexible bag" designate a bag or pouch made of walls of similar structure preferably assembled by welding. These walls may be made of a mono- or multilayer film including or not a barrier layer based on a barrier polymer like EVOH (ethylene vinyl alcohol polymer). Generally, these films may have an inner layer (in contact with the contents of the bag when filled) based on a polyolefin, preferably an ULDPE (ultra-low density polyethylene, pref. medical grade).

The bag may be of cylindrical shape although cylindrical flexible bags are not easily baffled and difficult to manufacture. A bag with a cubic or parallel-piped shape is preferable namely because it works as a baffled tank which enhances its mixing capacity.

The flexible bag according to the present invention comprises at least two facing walls. This means in fact that when said bag is empty, at least two portions of its wall(s) are in contact with each other by their internal surface i.e. their surface intended to be in contact with the contents of the bag.

The flexible bag according to the invention may be used to store, mix, handle (for any purpose whatsoever) a fluid. According to the invention, it has a functional part having at least a portion protruding inside of it i.e. extending in the volume defined by the bag's wall(s). This part is protruding from a wall of the tank. This is meant to encompass the cases where the part would be protruding from an angle and potentially damaging an opposite wall or angle. Also, the part must not necessarily by fixed on said wall or corner. It might merely rest on it or pass through an opening therein. If it is fixed to it, it may be by welding, riveting, clamping.

This protruding functional part may be any accessory required for at least one active function of the bag. The functional part is preferably chosen between a mixing device; a gas sparger; a dip tube; or a sensor for measurement of temperature pH, conductivity, turbidity, biomass, redox potential, dissolved oxygen or any other signal.

Although this accessory may have any shape or size, the present invention is advantageously applied to large parts so that the protective means can fulfil several functions as will be explained later on By "large" is meant having their biggest dimension in the range of the centimeters (e.g. up to 30 cm)

For instance, the present invention gives good results when the functional part is a mixing device which may either be a mere impeller protruding inside the bag or a more sophisticated system like the mixing dish from the HYCLONE MIXTAINER Bioprocessing System or the LEVTECH Disposable Mixing System, or even a combination of a mixing device and gas sparger, or any other part combining a mixing effect with another function.

Although any kind of mixing device may be used in a flexible bag, it is preferably a device including a magnetic impeller which is driven from the outside as explained above.

The present invention gives good results when the mixing device comprises a rotary magnetic impeller located in a compartment delimited by a wall, said mixing device further comprising:
  at least one liquid inlet opening located in a central area of the wall;
  at least one liquid outlet opening located in a peripheral area of the wall; and deflecting means that substantially alter the natural rotational direction of the liquid exiting the outlet opening.

These deflecting means and/or the wall of this mixing device might indeed comprise angles or other kinds of prominent parts which are susceptible to damage the wall of the bag facing said mixing device.

Besides, as set forth in a co-pending application, said mixing device is not necessarily secured to the bag when said bag is shipped and handled before use so that the cover of the invention may help (together with the vacuum generally applied to said bag) keeping said part substantially at the place where it should be fixed in use.

If said mixing device is secured to the bag, it may be by welding or by using at least one of the following:

magnets in extension arms susceptible to work with corresponding magnets disposed in the rigid container;
  at least two extension arms welded (or mechanically fixed in any other way) to at least two drains or two other rigid components of the bag.

The flexible bag according to the present invention comprises protective means on the wall (or the corner: see previously) opposite to the one where the functional part is located. These protective means may be integral with the bag's wall (for instance: they may consists in a part of the wall being of higher thickness) or they may be fixed to it. These protective means are preferably secured to the wall of the bag and even more specifically, they are preferably secured to an opening of said wall and more precisely: they are preferably welded or clamped on the periphery of the opening.

These means may be of any geometry allowing them to protect the protruding portion of the functional part. Preferably, they are in the shape of a cover having a cavity sized to accommodate the protruding portion of the functional part. Preferably, said cavity has a shape substantially matching the external shape of the protruding portion. The lower border of said cover is preferably secured from the inside (welded, clamped or fixed by any other means) to the periphery of said opening i.e. on the inner surface of the bag in order to avoid that the outer layer of the film would be in contact with the liquid. Nevertheless, it can be also secured from the outside of said periphery. In that embodiment, said securing is preferably performed before the final assembly of the bag.

In order to achieve leak tightness, the cover is preferably either welded or clamped (using a flange and a gasket) on the periphery of the opening.

Welding the cover to the outer periphery of the opening is preferred. To that end, said cover is preferably provided with a welding flange located at its periphery. In the case the functional part also comprises a welding flange, both flanges are preferably of a size and shape such that the flange of the cover rests on the flange of the functional part when the bag is empty. This allows a good distribution of the pressure between both flanges when the bag is positioned inside a rigid container.

To ensure the welding ability of the cover on the bag, said cover is preferably based on a material compatible with the material constituting the outer surface of the bag. Considering the layout of the industrial films set forth above, a polymer of ethylene is a good choice. Preferably, a HDPE (high density polyethylene) is used because other polymers like EVA (Ethylene Vinyl Acetate copolymer) or LDPE are not rigid enough.

This cover may be obtained by any method suitable for moulding plastic parts, preferably by injection moulding. Hence, injection moulding grades of the above mentioned polymers (more preferably: of HDPE) are preferably used.

The cover according to this embodiment of the invention comprises a cavity which is substantially matching the external shape of the protruding portion of the functional part. The terms "substantially matching" means in fact that the protruding portion fits (can be inserted) inside the cover and can be removed there from i.e. that it has smaller dimensions and an adequate shape to be able to be received (preferably completely) inside the cover.

In one embodiment, the protruding portion of the functional part does not fit tightly inside the cover so that there is no wear between the surfaces of both parts (except perhaps on their welding flanges or other substantially horizontal contact surface, if any) and this even with the usual manufacturing tolerances.

However, when the cover is used to fix the protruding part to a rigid container (or any other support/part), it may be preferable to fit both pieces more tightly at least on a portion thereof so that a torque exerted on the cover can easily be transmitted to the protruding portion of the part. In that embodiment, corresponding portions in relief may be provided on both parts which are in contact when the cover rests on the protruding portion of the functional part so that the torque transmission is improved.

Generally, the cover has a substantially constant wall thickness which depends on the mechanical resistance required.

As to its outer shape, it may be adapted to enhance the ease of handling of the bag and/or the fixation of the protruding part on a support. In that regard, it may be provided with an extension and/or its cavity may be extended upwards so that it acquires a prehensile shape.

The protective means of the bag according to the invention may be equipped with functional means for instance: with port(s) for entry/exit of liquid(s) or gas; with sensors or supports there for; with impeller (s) which may be lowered inside the bag once filled.

This functional means must of course be disposed/fixed on said means in a way such that they still allow the means to exert their protective function (i.e. allow the protruding portion to fit in the cavity of the cover, the case being).

The present invention also concerns a mixing system comprising a flexible bag as described above and a rigid container supporting said bag.

Preferably, according to that aspect of the invention, the functional part is a magnetic mixing device and the mixing system comprises a magnetic driver located outside the container, generally below its bottom.

In that embodiment, preferably, a portion of the flexible bag is sandwiched between at least a portion of the mixing device and a portion of the rigid container, these portions being generally part of the bottom wall of the bag and of the rigid container respectively. "Sandwiched" means that said portions are directly in contact and pressed against each other by gravity (if the mixing device rests on the bottom of the mixing bag and the container) and/or by any other means which preferably do not perforate the bag and the container (additional magnets for instance).

There is hence no intermediate connecting piece between the mixing device and the driver, or, in other terms: there is no direct mechanical connection between both elements. Instead, either they are both precisely located relative to the rigid container (first embodiment) or they are free to auto align themselves through the magnetic forces they both exert on each other (second embodiment).

By doing so, there is no need to provide the bag and the container with an opening, no need to manufacture an additional connecting piece and the use of said containers can be made standard.

The present invention gives good results with the second embodiment mentioned above and especially, when the mixing device is not (at least not firmly) secured to the flexible bag so that the cover can help keeping said mixing device substantially in place during storage and handling of the empty bag. The vacuum generally applied on said bag also helps in that regard.

In order to allow the mixing device to auto align itself with its driver, the flexible bag of that embodiment may comprise a positioning mechanism to position and maintain the mixing device only approximately at a given location (i.e. said device is not secured to its walls but free to move a little relative to it) when the bag is inserted inside the rigid container. This positioning mechanism may include welding tabs, bridges or any other fixation part (like a double annular wall for instance) fixed on the bag wherein the mixing device is retained but can move freely (relative to the bag) in at least one direction of space (and preferably, in the three directions of space) while remaining in a given perimeter (surrounding the driver when the bag is inserted in the rigid container).

This embodiment is advantageous because the mixing device will align itself automatically with its driver (through the magnetic forces they both exert on each other) so that there is no need for a perfect mechanical relative alignment between the mixing device, the driver and the rigid container. This embodiment is also advantageous because there is no need for the welding of a (potentially) large circumferential part, what presents quality issues as far as leakages are concerned.

As explained above, the protective means of the bag according to the invention may consist in a cover comprising a portion in relief cooperating with a matching portion in relief on the functional part so that said part can be fixed on the container using the cover.

Accordingly, the present invention also concerns a method for fixing a flexible bag as described above inside a rigid container, wherein the cover and the functional part bear complementary relieves and according to which the functional part is fixed to the container using the cover which is then decoupled from said part before filling the bag.

Other characteristics and advantages of the invention will appear more clearly in the light of the following description of a particular non-limiting embodiment of the invention, while referring to the figures attached (FIGS. 1, 2a, and 2b).

FIG. 1 shows in detail a mixing device inside the cavity of a protective cover, FIG. 2a, a schematic view of said mixing device and cover in an empty flexible bag and FIG. 2b in said bag filled with liquid.

FIG. 1 is an axial cut (i.e. a cut through a plane comprising the symmetry axis) through a mixing device (1, 2) provided with its protective cover (3). Both parts are provided with a welding flange (1', 3') intended to be welded on a flexible bag (not shown) respectively on the inner surface of the bottom wall (under surface of flange 1') and on the inner surface of the top wall, on the periphery of an opening there through (upper surface of flange 3').

The mixing device illustrated comprised a base (1), a cover (2) and a magnetic impeller (5) rotating on a bearing (4) supported by a protrusion (6) of the base (1).

The cover (3) has an internal volume or cavity substantially matching the external shape of the mixing device (1, 2) at its base but having a chimney or a dome shaped extension (7) at its top providing a grip enhancing the ease of handling of the cover and of the flexible bag for which it is intended. This extension can be used to integrate functional means, like ports for inlets or outlets of liquids or gases, probes, impellers or the like.

The cover (3) has been manufactured by injection moulding and it shows a substantially uniform wall thickness with just a slight increase in the neighbourhood of its injection point (8). It is made of an injection moulding grade of HDPE.

FIGS. 2a and 2b illustrate how the cover (3) is welded to the periphery of an opening into a bag comprising 2 facing walls (9, 9'), one of which (9) bearing a protective cover for the mixing device (1, 2) located on its facing wall (9). This welding is made between the upper surface of the cover's welding flange (3') and the inner periphery of the opening in the bag. It also illustrates how the mixing device is welded to the bottom of the bag (9') by the lower surface of its welding flange (1'), and how the 2 parts fit to each other when the bag is empty and are separate when the bag is empty.

Although the preferred embodiments of the invention have been disclosed for illustrative purpose, those skilled in the art will appreciate that various modifications, additions or substitutions are possible, without departing from the scope and spirit of the invention as disclosed in the accompanying claims.

The invention claimed is:

1. A flexible bag comprising: at least a first wall and a second wall, said at least first and second walls defining an interior of said flexible bag, said second wall facing said first wall when said flexible bag is folded; and a functional part, at least a portion of said functional part protruding from said first wall into said interior of said flexible bag; wherein said second wall comprises a protective cover having a cavity which accommodates said protruding portion of said functional part when said flexible bag is folded and which does not accommodate said protruding portion of said functional part when said flexible bag is unfolded, wherein said protruding portion of said functional part has a shape, and wherein said cavity is substantially matching said shape of said protruding portion of said functional part.

2. The flexible bag of claim 1, wherein: said protruding portion of said functional part and said protective cover have mating surfaces; and said protruding portion of said functional part does not fit tightly inside said protective cover so that there is no wear between said mating surfaces.

3. The flexible bag of claim 1, wherein said protruding portion of said functional part fits tightly in at least a portion of said protective cover such that a torque exerted on said protective cover can be transmitted to said protruding portion of said functional part.

4. The flexible bag of claim 1, wherein said protective cover is configured with at least one of an extension and a shape adapted for grasping.

5. The flexible bag of claim 1, wherein said functional part comprises one of a mixing device, a gas sparger, a dip tube, and a sensor.

6. The flexible bag of claim 5, wherein said functional part comprises a mixing device, said mixing device in turn comprising a rotary magnetic impeller.

7. The flexible bag of claim 6, wherein said mixing device is retained by said protective cover.

8. The flexible bag of claim 1, wherein said second wall has an opening therein, and wherein said protective cover is secured within said opening in said second wall from said interior of said flexible bag.

9. The flexible bag of claim 8, wherein said opening in said second wall has a periphery and wherein said protective cover is secured within said opening in said second wall via at least one of welding to said periphery of said opening and clamping to said periphery of said opening.

10. The flexible bag of claim 9, wherein said protective cover comprises a peripheral flange, and wherein said protective cover is secured within said opening in said second wall via welding said peripheral flange to said periphery of said opening.

11. The flexible bag of claim 10, wherein: said functional part comprises a welding flange; said peripheral flange of said protective cover and said welding flange of said functional part are configured and dimensioned such that said peripheral flange of said protective cover rests on said welding flange of said functional part when said flexible bag is empty.

12. The flexible bag of claim 1, wherein said protective cover is injection molded from an injection molding grade of high density polyethylene.

13. The flexible bag of claim 1, wherein said protective cover comprises a functional portion.

14. The flexible bag of claim 1, wherein said functional portion comprises at least one of a fluid port, a sensor, a sensor support, and an impeller.

* * * * *